United States Patent [19]

Losier et al.

[11] Patent Number: 5,458,740

[45] Date of Patent: Oct. 17, 1995

[54] PROCESS FOR THE PURIFICATION OF CRUDE CAPROLACTAM

[75] Inventors: Thomas P. Losier; Donald R. Johnson, both of Lake Jackson, Tex.; Hugo Fuchs, Ludwigshafen, Germany; Gerald Neubauer, Weinheim, Germany; Josef Ritz, Ludwigshafen, Germany

[73] Assignee: BASF Corporation, Mt. Olive, N.J.

[21] Appl. No.: 205,979

[22] Filed: Mar. 4, 1994

[51] Int. Cl.⁶ .................................................. B01D 3/34
[52] U.S. Cl. ........................... 203/34; 159/47.3; 203/14; 203/35; 203/73; 203/DIG. 25; 540/540
[58] Field of Search ..................... 203/34, 14, 35, 203/38, 80, 73, DIG. 25, 15, 91, DIG. 16; 540/540, 464; 159/47.3, DIG. 19

[56] References Cited

U.S. PATENT DOCUMENTS

| | | | |
|---|---|---|---|
| 3,502,676 | 3/1970 | Becke et al. | 544/347 |
| 4,457,807 | 7/1984 | Rulkens et al. | 203/72 |
| 5,169,870 | 12/1992 | Corbin et al. | 521/49.8 |

FOREIGN PATENT DOCUMENTS

| | | |
|---|---|---|
| 5310 | 6/1953 | Germany . |
| 950726 | 9/1956 | Germany . |
| 1272287 | 7/1968 | Germany . |
| 2801256 | 7/1978 | Germany . |
| 2926279 | 1/1981 | Germany . |

OTHER PUBLICATIONS

CA 103: 215940.

*Primary Examiner*—Virginia Manoharan
*Attorney, Agent, or Firm*—Nixon & Vanderhye

[57] ABSTRACT

A process for the purification of caprolactam from crude caprolactam by distilling the crude caprolactam in the presence of an anorganic or organic acid.

5 Claims, No Drawings

PROCESS FOR THE PURIFICATION OF CRUDE CAPROLACTAM

FIELD OF THE INVENTION

The present invention relates to a process for the purification of crude caprolactam, more specifically it relates to the purification of crude caprolactam by distillation in the presence of an acid.

BACKGROUND OF THE INVENTION

There are a multiplicity of sources for crude caprolactam like wastewater from the manufacture and thermoplastic processing of polycaprolactam (nylon 6) or catalytic cracking of oligomers and polymers of caprolactam.

Extractions of wastewater from the manufacture of polycaprolactam contain oligomers, polymers and monomers of epsilon caprolactam, are hereinafter referred to as caprolactam. There are several methods known for the recovery of caprolactam from these extractions, which contain oligomers and polymers of caprolactam. DE-A 950,726 and DE-A 1,272,287 disclose a depolymerization of polycaprolactam with phosphoric acid. The crude caprolactam is distilled by a steam distillation. The distilled caprolactam does not meet all quality requirements and the phosphoric acid containing residues are difficult to dispose.

DD-A 5310 discloses a depolymerization of polycaprolactam with sodium hydroxide.

U.S. Pat. No. 5,169,870 discloses a process for the recovery of epsilon caprolactam from nylon 6 carpet by catalytical depolymerization of the polycaprolactam, followed by vacuum distillation.

Object of the present invention was to provide a process for the purification of crude caprolactam which produces caprolactam in high purity and yield.

SUMMARY OF THE INVENTION

The object of the present invention could be achieved by a process for the purification of crude caprolactam which comprises distilling the crude caprolactam in the presence of an acid.

DETAILED DESCRIPTION OF THE INVENTION

One source for crude caprolactam is the wastewater from the polymerization of caprolactam. During the manufacture of polycaprolactam, wastewater is produced which contains from about 1 to 20% by weight of solids, preferably 2 to 10, most preferred 3 to 8% by weight. The solids contain from about 1 to about 70% by weight of caprolactam, from about 0.1 to 10% by weight of oligomers of caprolactam and from about 1 to about 99% by weight of polycaprolactam, based on the total amount of solids.

This wastewater may be concentrated by distilling off the water to a solid concentration of from about 50 to about 90% by weight, preferably 60–85% by weight.

The oligomers and polymers of the caprolactam are catalytically cracked by introducing the wastewater to a fluidized bed of aluminum oxide at a temperature of from about 270° C. to about 400° C., preferably from about 290 to 360°. The introduction into the fluidized bed reactor may occur through a nozzle with or without an inert gas.

Suitable aluminum oxides are alpha or gamma aluminum oxide, preferred is gamma-aluminum oxide as catalyst. The catalyst is held in the form of a fluidized bed by an inert gas like carbon dioxide, argon, nitrogen, preferred is nitrogen. The inert gas is introduced into the fluidized bed reactor at a temperature of from about 290° C. to about 400° C.

The gas mixture which exits the fluidized bed reactor is condensed to an aqueous solution of crude caprolactam.

The water of the aqueous solution of crude caprolactam is evaporated by distillation or thin film evaporation.

Suitable thin film evaporators are horizontal units with a tampered rotor, using steam jets to provide vacuum. They consist of a dehydrator to remove water, a first distillation unit, and a second distillation unit and they are commercially available from for example Artisan Industries.

After the water has been removed, the remaining crude caprolactam contains from about 85 to about 99% by weight, preferably from about 90 to about 99% by weight, most preferred from about 95 to about 99% by weight of caprolactam, based on the total amount of crude caprolactam.

Another source for crude caprolactam is the wastewater of thermoplastic processing of polycaprolactam, which contains after distilling off the water from about 85 to about 99% by weight preferably from about 90 to about 99% by weight of caprolactam.

Another source for crude caprolactam is the catalytic cracking of polycaprolactam from sources like nylon 6 carpet, waste strands or other nylon 6 parts in accordance with the process described above or the process disclosed in U.S. Pat. No. 5,169,870.

The crude caprolactam from the different sources described above is distilled according to the present invention in the presence of an inorganic acid like sulfuric acid or oleum or an organic acid like p-toluolsulfonic acid or an ion exchange resin like a crosslinked polystyrene with sulfonic acid groups. Preferred is sulfuric acid. A suitable amount of acid ranges from about 0.01 to about 5% by weight, preferably from about 0.1 to about 1% by weight based on the crude caprolactam. The amount of ion exchange resin is from about 1 to about 30 by weight, preferably from about 2 to about 10% by weight, based on the crude caprolactam.

The distillation is usually performed under a pressure of from about 50 Pa to about 3000 Pa, preferably from about 100 to about 2000 Pa. The temperature is from about 100° to about 180° C., preferably from about 120° to about 150° C.

The distillation consists of from about 95 to about 99% by weight caprolactam, preferably from about 96 to about 99.9% by weight The remaining sump after the distillation may be neutralized with ammonia, NaOH or CaO and incinerated.

EXAMPLE 1: (COMPARATIVE)

500 g of crude caprolactam, obtained by depolymerization of polycaprolactam, which has been recovered from chip wash water, with a solid content of 95% by weight, which consists of 95% by weight of caprolactam and 5% by weight of water. The crude caprolactam is heated to between 165°–180° C. and then distilled at 666–1066 Pa. 450 g of a colorless distillate is obtained. The distillate was 99% by weight caprolactam with the properties shown in Table I.

EXAMPLE 2

500 g of crude caprolactam, obtained by depolymerization of polycaprolactam, which has been recovered from chip wash water, with a solid content of 95% by weight, which consists of 95% by weight of caprolactam and 5% by weight of water, is mixed with 1% by weight of 95%–98% sulfuric acid. The mixture is heated to between 165°–180° C. and then distilled at 666–1066 Pa. 450 g of a colorless distillate is obtained. The distillate was 99% by weight caprolactam with the properties shown in Table I.

EXAMPLE 3

500 g of crude caprolactam, obtained by depolymerization of polycaprolactam, which has been recovered from chip wash water, with a solid content of 95% by weight, which consists of 95% by weight of caprolactam and 5% by weight of water, is mixed with 0.1% by weight of 95%–98 sulfuric acid. The mixture is heated to between 165°–180° C. and then distilled at 5–8 mm Hg. (666– 1066Pa). 450 g of a colorless distillate are obtained. The distillate was 99% by weight of a colorless distillate are obtained. The distillate was 99% by weight caprolactam with the properties shown in Table I.

TABLE I

| Examples | Permanganate Number 1) | Fluorescence Number 2) |
|---|---|---|
| Crude Caprolactam | 30.5 | 26827 |
| 1 (Comparative) | 4.5 | 307 |
| 2 | 4.6 | 226 |
| 3 | 2.1 | 247 |

It is seen from the data in Table I that the quality is improved due to the purification using acid.

1) Determination of Permanganate Absorbance Number in Caprolactam

The permanganate reduced by caprolactam is determined photometrically. Equal amounts of a 0.01 N potassium permanganate solution are added to a 3% (m/m) aqueous caprolactam solution and to a distilled, oxygen free, pH 6.2–6.5, water blank. After 10 minutes, the absorbance of the solutions is measured at $\lambda=420$ nm. The permanganate absorbance number is calculated from:

$$PAN=(A_1-A_0)*100/3$$

$A_1$=Absorbance number of the permanganated caprolactam solution against water.

$A_0$=Absorbance of the permanganated water blank solution against water

2) Determination of Fluorescence Number of Caprolactam

The fluorescence number is determined by scanning the prepared caprolactam sample on a Simadzu RF-5000 spectrometer. The wavelength from 400 nm to 650 nm is used. The sample is prepared by dissolving 5 grams of caprolactam in 43 grams of deionized water. A 1 cm quartz cell is filled with the sample solution. The cell is placed in the instrument and held for 1 minutes for stabilization. The sample is scanned from $\lambda=374$ nm to $\lambda=600$ nm. The peak centerd at 430 nm is the quantitative measure of the sample fluorescence. The area between 400 nm and 490 nm is integrated. This number is reported as the fluorescence number.

We claim:

1. A process for recovering and purifying crude caprolactam from crude caprolactam-containing wastewaters consisting essentially of the steps:

(a) obtaining a wastewater stream containing crude caprolactam from at least one process which by-produces a crude caprolactam-containing wastewater stream selected from caprolactam polymerization, catalytic cracking of polymers and oligomers of caprolactam, and thermoplastic processing of polycaprolactam;

(b) mixing the crude caprolactam-containing wastewater stream with between about 0.01 to 5% by weight, based on the crude caprolactam in the wastewater stream, of an acid;

(c) subjecting the mixture of crude caprolactam-containing wastewater stream and acid obtained according to step (b) to purification distillation at a temperature of between about 100 to about 180° C. and a pressure of between about 50 to about 3000 Pa;

(d) obtaining purified crude caprolactam as a distillate from step (c); and (e) neutralizing distillation bottoms obtained from step (c), and then incinerating said neutralized distillation bottoms.

2. The process as in claim 1, wherein prior to step (b), there is practiced the step of ($a_1$) concentrating the crude caprolactam in the wastewater stream to between about 85 to about 95% by weight.

3. The process as in claim 2, wherein said step ($a_1$) includes evaporating water from said crude caprolactam-containing wastewater stream.

4. The process as in claim 1, wherein the acid is at least one inorganic acid selected from the group consisting of sulfuric acid, and oleum.

5. The process as in claim 1, wherein the acid is at least one organic acid selected from the group consisting of p-toluolsulfonic acid and an ion exchange resin having sulfonic acid groups.

* * * * *